US00PP19948P2

(12) United States Plant Patent
Kools

(10) Patent No.: US PP19,948 P2
(45) Date of Patent: Apr. 21, 2009

(54) ***CHAMAECYPARIS* PLANT NAMED 'LUCAS'**

(50) Latin Name: *Chamaecyparis obtusa*
Varietal Denomination: Lucas

(75) Inventor: Cornelius Petrus Franciscus Kools, Deurne (NL)

(73) Assignee: Witteman + Co., Hillegom (NL)

( * ) Notice: Subject to any disclaimer, the term of this patent is extended or adjusted under 35 U.S.C. 154(b) by 0 days.

(21) Appl. No.: 12/151,753

(22) Filed: May 8, 2008

(51) Int. Cl.
*A01H 5/00* (2006.01)

(52) U.S. Cl. ..... Plt./214
(58) Field of Classification Search ..... Plt./214
See application file for complete search history.

*Primary Examiner*—Annette H Para
*Assistant Examiner*—Georgia Helmer
(74) *Attorney, Agent, or Firm*—C. A. Whealy

(57) ABSTRACT

A new and distinct cultivar of *Chamaecyparis* plant named 'Lucas', characterized by its semi-dwarf and hemispherical plant form; green, yellow green to light yellow green-colored leaves; and winter hardy.

2 Drawing Sheets

Botanical designation: *Chamaecyparis obtusa.*
Cultivar denomination: 'LUCAS'.

BACKGROUND OF THE INVENTION

The present Invention relates to a new and distinct cultivar of *Chamaecyparis,* botanically known as *Chamaecyparis obtusa,* and hereinafter referred to by the name 'Lucas'.

The new *Chamaecyparis* originated from an open-pollination in 1997 in Deurne, The Netherlands, of *Chamaecyparis obtusa* 'Lutea Nova', not patented, as the female, or seed, parent with an unknown selection of *Chamaecyparis obtusa* as the male, or pollen, parent. The new *Chamaecyparis* was discovered and selected by the Inventor as a single plant within the progeny of the stated open-pollination in a controlled greenhouse environment in Deurne, The Netherlands in 1998.

Asexual reproduction of the new *Chamaecyparis* by cuttings in a controlled greenhouse environment in Deurne, The Netherlands since 1999, has shown that the unique features of this new *Chamaecyparis* are stable and reproduced true to type in successive generations.

SUMMARY OF THE INVENTION

Plants of the cultivar Lucas have not been observed under all possible environmental conditions. The phenotype may vary somewhat with variations in environment and culture such as temperature and light intensity without, however, any variance in genotype.

The following traits have been repeatedly observed and are determined to be the unique characteristics of the new *Chamaecyparis.* These characteristics in combination distinguish 'Lucas' as a new and distinct cultivar of *Chamaecyparis:*

1. Semi-dwarf and hemispherical plant form.
2. Green, yellow green to light yellow green-colored leaves.
3. Winter hardy.

Plants of the new *Chamaecyparis* are most similar to plants of the female parent, 'Lutea Nova'. Plants of the new

*Chamaecyparis* differ from plants of 'Lutea Nova' in the following characteristics:

1. Plants of the new *Chamaecyparis* are more compact than plants of 'Lutea Nova'.
2. Plants of the new *Chamaecyparis* are more hemispherical and uniform than plants of 'Lutea Nova'.
3. Plants of the new *Chamaecyparis* and 'Lutea Nova' differ in leaf color as plants of 'Lutea Nova' have green-colored leaves.

Plants of the new *Chamaecyparis* can also be compared to plants of *Chamaecyparis obtusa* 'Crippsii', not patented. Plants of the new *Chamaecyparis* differ from plants of 'Crippsii' in the following characteristics:

1. Plants of the new *Chamaecyparis* are more upright than plants of 'Crippsii'.
2. Plants of the new *Chamaecyparis* are more irregularly branched than plants of 'Crippsii'.
3. Plants of the new *Chamaecyparis* and 'Crippsii' differ in leaf color as plants of 'Crippsii;' have green-colored leaves.

BRIEF DESCRIPTION OF THE PHOTOGRAPHS

The accompanying colored photographs illustrate the overall appearance of the new *Chamaecyparis,* showing the colors as true as it is reasonably possible to obtain in colored reproductions of this type. Colors in the photographs may differ slightly from the color values cited in the detailed botanical description which accurately describe the colors of the new *Chamaecyparis.*

The photograph on the first sheet is a side perspective view of a typical plant of 'Lucas' grown in a container.

The photograph on the second sheet is a close-up view of the foliage of a typical plant of 'Lucas'.

DETAILED BOTANICAL DESCRIPTION

Plants used for the aforementioned photographs and following observations and measurements were grown in Deurne, The Netherlands during the summer and early autumn in an outdoor nursery and under conditions which approximate commercial *Chamaecvparis* production. During the production of the plants, day temperatures ranged from 10° C. to 28° C. and night temperatures ranged from 4° C. to 15° C. Plants had been growing for five years when the photographs and description were taken. In the following description, color references are made to The Royal Horticultural Society Colour Chart, 2001 Edition, except where general terms of ordinary dictionary significance are used.

Botanical classification: *Chamaecyparis obtusa* 'Lucas'.

Parentage:

*Female, or seed, parent.*—*Chamaecyparis obtusa* 'Lutea Nova', not patented.

*Male, or pollen, parent.*—Unknown selection of *Chamaecyparis obtusa,* not patented.

Propagation:

*Type.*—By cuttings.

*Time to initiate roots.*—About two months at 15° C. to 25° C.

*Time to produce a rooted cutting.*—About 250 days at 15° C. to 25C.

*Root description.*—Fibrous, fleshy; white to brown in color.

*Rooting habit.*—Moderate branching; moderately dense.

Plant description:

*Form/growth habit.*—Semi-dwarf and hemispherical to broadly pyramidal perennial evergreen shrub, globular; upright to outwardly spreading plant habit. Moderately vigorous growth habit.

*Branching habit.*—Freely branching with about 30 lateral branches developing per plant. Branches mostly horizontal to arching. Plants maintain their lower branches and foliage at the soil level.

*Plant height.*—About 44.2 cm.

*Plant diameter.*—About 64.4 cm.

*Lateral branch description.*—Length: About 33.9 cm. Diameter: About 3.5 mm. Internode length: About 1.6 cm. Texture: Smooth, scaly. Strength: Strong. Color, developing: Close to 144A. Color, mature: Close to N199C to N199D.

*Leaf description.*—Appearance/arrangement: Flattened and appressed; opposite; sessile. Length: About 7 mm. Width: About 2 mm. Shape: Narrowly oblanceolate, scale-like. Apex: Acute. Base: Cuneate. Margin: Entire. Texture, upper and lower surface: Smooth, glabrous. Venation pattern: Linear. Fragrance: Cedar-like. Color: Developing leaves, upper and lower surfaces: Initially 143B becoming close to 144A with development. Fully expanded leaves, upper surface: Close to 4D becoming closer to 150D with development; venation, similar to lamina. Fully expanded leaves, lower surface: Close to 138A to 138B; venation, similar to lamina.

*Cone description.*—Cone development has not been observed.

Disease/pest resistance: Plants of the new *Chamaecyparis* have not been noted to be resistant to pathogens or pests common to *Chamaecyparis.*

Weather tolerance: Plants of the new *Chamaecyparis* have been observed to be tolerant to drought, rain, wind and temperatures ranging from about −17° C. to about 35° C.

It is claimed:

1. A new and distinct *Chamaecyparis* plant named 'Lucas' as illustrated and described.

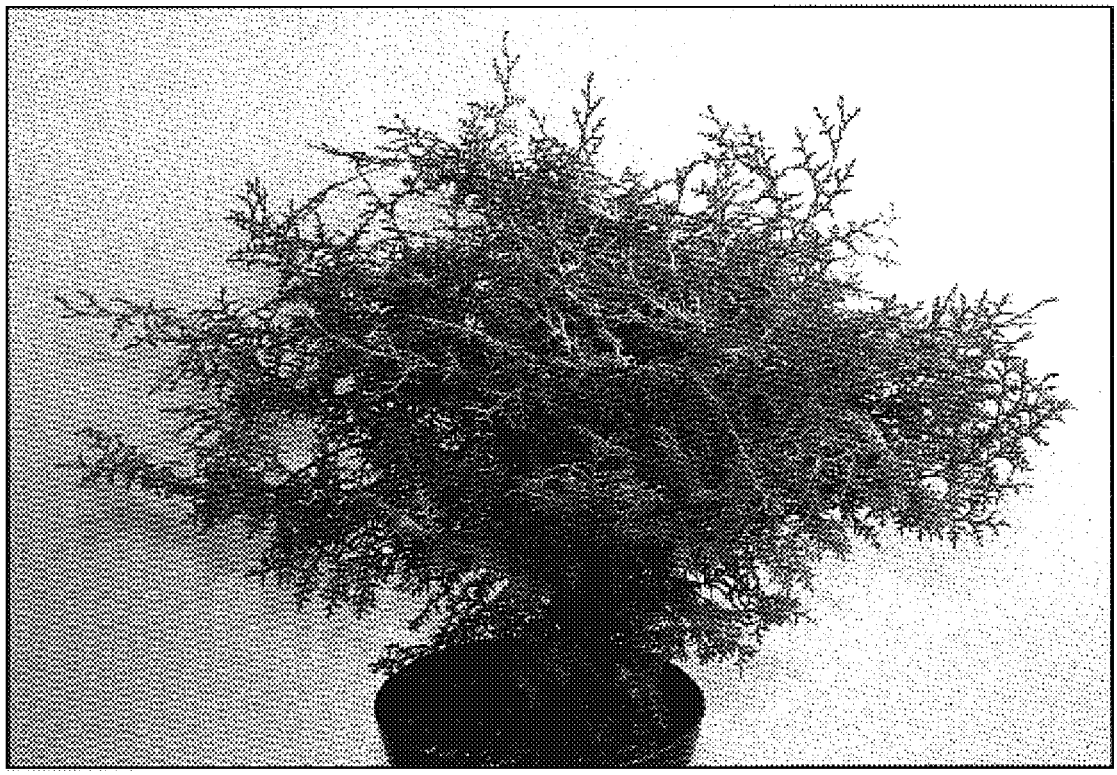

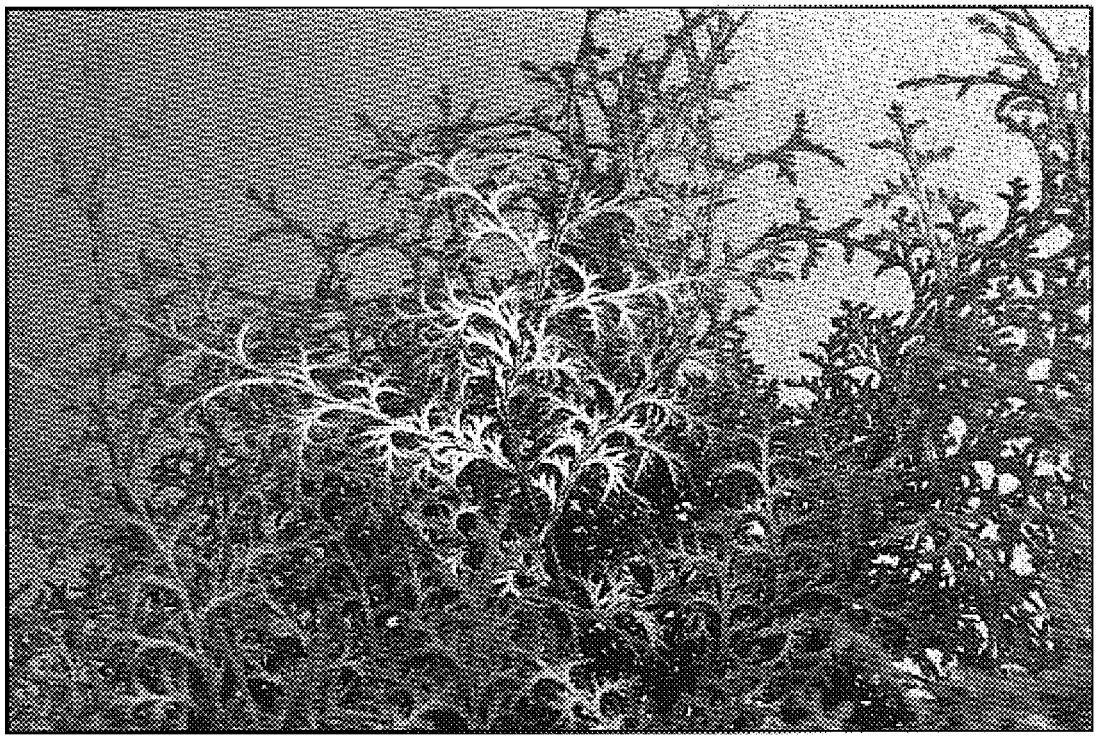

* * * * *